United States Patent
Bianchini et al.

(10) Patent No.: US 11,155,647 B2
(45) Date of Patent: Oct. 26, 2021

(54) WATER-SOLUBLE POLYSACCHARIDE DERIVATIVES, PROCESS FOR THEIR PREPARATION, AND THEIR USES

(71) Applicant: JOINTHERAPEUTICS S.R.L., Como (IT)

(72) Inventors: Giulio Bianchini, Como (IT); Lanfranco Callegaro, Como (IT)

(73) Assignee: JOINTHERAPEUTICS S.R.L., Como (IT)

(*) Notice: Subject to any disclaimer, the term of this patent is extended or adjusted under 35 U.S.C. 154(b) by 0 days.

(21) Appl. No.: 16/616,731

(22) PCT Filed: May 29, 2018

(86) PCT No.: PCT/IB2018/053790
§ 371 (c)(1),
(2) Date: Nov. 25, 2019

(87) PCT Pub. No.: WO2018/220514
PCT Pub. Date: Dec. 6, 2018

(65) Prior Publication Data
US 2020/0407468 A1    Dec. 31, 2020

(30) Foreign Application Priority Data
Jun. 1, 2017 (IT) .......... 102017000060530

(51) Int. Cl.
| | | |
|---|---|---|
| C08B 37/08 | (2006.01) |
| A61K 31/722 | (2006.01) |
| A61K 31/734 | (2006.01) |
| A61K 31/737 | (2006.01) |
| A61K 31/765 | (2006.01) |
| A61K 33/42 | (2006.01) |
| A61K 38/39 | (2006.01) |

(52) U.S. Cl.
CPC .......... *C08B 37/003* (2013.01); *A61K 31/722* (2013.01); *A61K 31/734* (2013.01); *A61K 31/737* (2013.01); *A61K 31/765* (2013.01); *A61K 33/42* (2013.01); *A61K 38/39* (2013.01); *C08J 2305/08* (2013.01); *C08J 2405/08* (2013.01)

(58) Field of Classification Search
None
See application file for complete search history.

(56) References Cited

U.S. PATENT DOCUMENTS
2012/0058536 A1    3/2012    Ruda et al.

FOREIGN PATENT DOCUMENTS
| WO | 2002040055 A2 | 5/2002 |
| WO | 2007135114 A1 | 11/2007 |
| WO | 2017211776 A1 | 12/2017 |

OTHER PUBLICATIONS

D'Amelio, J. Phys. Chem. B, 2013, 117, 13578-13587. (Year: 2013).*
Mertins, Langmuir 2013, 29, 14545-14551. (Year: 2013).*
Kim et al., "Chitosan and its derivatives for tissue engineering applications", Biotechnology Advances, vol. 26, No. 1, Nov. 23, 2007, pp. 1-21.
Search Report and Written Opinion of PCT/IB2018/053790 dated Jul. 30, 2018.
Yalpani M et al., "Some chemical and analytical aspects of polysaccharide modifications. 3. Formation of branched-chain, soluble chitosan derivatives", Macromolecules, American Chemical Society US, vol. 17, Jan. 1, 1984, pp. 272-281.

* cited by examiner

Primary Examiner — Layla D Berry
(74) Attorney, Agent, or Firm — Silvia Salvadori, P.C.; Silvia Salvadori

(57) ABSTRACT

A neutral salt consisting of a polyaminosaccharide cation and an anion, as well as a procedure for the preparation of the neutral salt and uses thereof as a biomaterial and as an ingredient in pharmaceutical compositions are disclosed. Indeed, said neutral salt has surprisingly exhibited high water-solubility and high purity, the preparation procedure having minimised the content of high-risk contaminants in the final product and reduced reaction and purification times.

19 Claims, No Drawings

WATER-SOLUBLE POLYSACCHARIDE DERIVATIVES, PROCESS FOR THEIR PREPARATION, AND THEIR USES

This application is a U.S. national stage of PCT/IB2018/053790 filed on 29 May 2018, which claims priority to and the benefit of Italian Application No. 102017000160530 filed on 01 Jun. 2017, the contents of which are incorporated herein by reference in their entireties.

FIELD OF THE INVENTION

The present invention relates to a neutral salt consisting of a polyaminosaccharide cation and an anion, as well as a process for the preparation of the neutral salt and its uses as a biomaterial and as an ingredient in pharmaceutical compositions.

Indeed, the neutral salt according to the invention has surprisingly exhibited high water-solubility and high purity, since a preparation process has been developed that minimises the content of high-risk contaminants in the final product, reduces reaction and purification times, and facilitates modification of the degree of substitution.

BACKGROUND ART

Chitin and chitosan are two polysaccharides which are both very commonplace in the animal and fungi kingdoms. From a chemical point of view, chitin is a polysaccharide consisting of multiple units of N-acetylglucosamine (N-acetyl-D-glucosamine) linked by a β-1.4 type bond. Naturally occurring chitin typically has approximately 15% of the repeating units deacetylated to the corresponding glucosamine (D-glucosamine) and is often found in the presence of chitosan, i.e. the analogous polysaccharide corresponding to high degrees of deacetylation (>60%). The deacetylation of the repeating unit N-acetylglucosamine to glucosamine makes a primary amino group available which gives basic properties to the polymer (chitosan pKa≈6.3). The typical solubility profile of chitin and chitosan (i.e. they are practically insoluble in water and in common organic solvents) limits their potential industrial applications. In this regard, precise protocols have been identified for the solubilisation of these polysaccharides in solutions of acetic acid, or other acids, an inevitable side effect of which—however—is hydrolysis of the polymer. Improvements in the solubility profile of polysaccharides can be obtained by derivatisation reactions aimed at achieving branching of the main chain, which results in the reduction of the intermolecular interactions which are often responsible for the low solubility profile. However, the isolation of these derivatives which entails purification through dialysis and/or gel permeation chromatography (GPC) or entails the use of a reducing agent containing the cyanide ion together with purification through dialysis in the presence of sodium azide, as a bacteriostatic agent, contributes to a pollutants' profile of the derivative, which is clearly unacceptable from a medical point of view.

WO 2017/211776 A1 mentions a compound called chitlac hydrochloride, wherein chitlac is characterised by a degree of lactose substitution of between 50 and 70% and is obtained from a 200-400 kDa chitosan with a degree of residual acetylation of approximately 15%. An object of the present invention is therefore to provide a product which increases the industrial applications of chitin and chitosan, by improving the solubility profile thereof, while also improving the acceptability profile thereof from a medical and a pharmaceutical viewpoint.

SUMMARY OF THE INVENTION

Said object has been achieved by a neutral salt consisting of a polyaminosaccharide cation and an anion, as stated in claim 1.

In another aspect, the present invention concerns a process for the preparation of the neutral salt consisting of a polyaminosaccharide cation and an anion.

In a further aspect, the present invention concerns the use of said neutral salt as a biomaterial or a scaffold for cell growth, in the treatment of orthopaedic diseases.

In a still further aspect, the present invention concerns the use of said neutral salt as a biomaterial or a scaffold for cell growth, in plastic-cosmetic surgery, haemodialysis, cardiology, angiology, ophthalmology, otolaryngology, odontology, gynaecology, urology, dermatology, and tissue repair.

In another aspect, the present invention relates to a pharmaceutical composition comprising a bioactive substance and at least one neutral salt consisting of a polyaminosaccharide cation and an anion.

In a further aspect, the present invention relates to the use of said pharmaceutical composition in the treatment of orthopaedic diseases.

For the purposes of the present invention, the term "orthopaedic disease" refers to a disease affecting the musculo-skeletal system, such as osteoarticular disease, muscular disease, ligament disease, and tendon disease.

In a still further aspect, the present invention concerns the use of said pharmaceutical composition in plastic-cosmetic surgery, haemodialysis, cardiology, angiology, ophthalmology, otolaryngology, odontology, gynaecology, urology, dermatology, and tissue repair.

As will become clear in the following detailed description and embodiments provided by way of non-limiting examples, the neutral salt according to the invention has surprisingly exhibited high water-solubility and high purity, since a preparation process has been developed that minimises the content of high-risk contaminants in the final product, reduces reaction and purification times, and facilitates modification of the degree of substitution.

DETAILED DESCRIPTION OF THE INVENTION

The invention therefore relates to a neutral salt consisting of a polyaminosaccharide cation and an anion, wherein the polyaminosaccharide cation consists of the following three repeating units:

a) up to 25% of

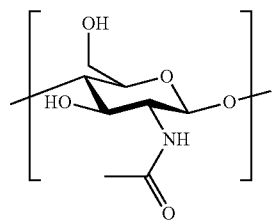

b) less than 65% of c) up to 90% of

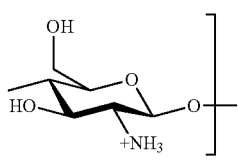

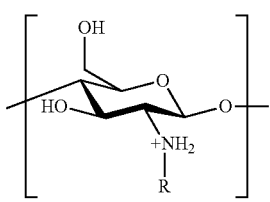

wherein R is an aldose or ketose moiety,
and
wherein the anion is monovalent, bivalent or trivalent.

Indeed, it has surprisingly been found that the neutral salt according to the invention reaches a high solubility in water in periods of time drastically reduced, while also being suitable for pharmaceutical and medical applications.

The definition of "neutral salt" is meant to include all the polymorphic forms, either amorphous or crystalline, or co-crystalline, as well as the anhydrous, hydrated, and solvate forms.

The repeating units b) and c) have been shown above as having the positive charge on the nitrogen atom, however, other forms of conjugated acid, in equilibrium with the most likely ammonium form shown, are not excluded.

Preferably, R is a moiety of formula (1):

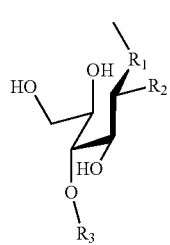

wherein $R_1$ is —$CH_2$— or —CO—,
$R_2$ is —OH, or —NHCOCH$_3$,
$R_3$ is H, monosaccharide, disaccharide, or oligosaccharide,
or R is a moiety of formula (2):

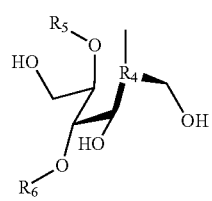

$R_4$ is —CH—,
$R_5$ and $R_6$ are, independently of each other, H, monosaccharide, disaccharide, or oligosaccharide.

Preferably, $R_3$, $R_5$ and $R_6$ are, independently of one another, H, glucose, galactose, arabinose, xylose, mannose, lactose, trealose, gentiobiose, cellobiose, cellotriose, maltose, maltotriose, chitobiose, chitotriose, mannobiose, melibiose, fructose, N-acetyl glucosamine, N-acetylgalactosamine, or a combination thereof.

More preferably, $R_3$ is H, glucose, galactose, mannose, N-acetylglucosamine, N-acetylgalactosamine, or a combination thereof.

In particularly preferred embodiments, R is a moiety of lactose or galactose.

Preferably, in the polyaminosaccharide cation, the repeating unit a) is present in a percentage of 5% to 20%.

More preferably, in the polyaminosaccharide cation, the repeating unit a) is present in a percentage of 7% to 18%.

Preferably, in the polyaminosaccharide cation, the repeating unit b) is present in a percentage of 5% to 45%.

More preferably, in the polyaminosaccharide cation, the repeating unit b) is present in a percentage of 20% to 40%.

Preferably, in the polyaminosaccharide cation, the repeating unit c) is present in a percentage of 45% to 90%.

More preferably, in the polyaminosaccharide cation, the repeating unit c) is present in a percentage of 50% to 70%.

In preferred embodiments, the polyaminosaccharide cation consists of:
5%-20% repeating unit a), 5%-45% repeating unit b), and 45%-90% repeating unit c).

In more preferred embodiments, the polyaminosaccharide cation consists of: 7%-18% repeating unit a), 20%-40% repeating unit b), and 50%-70% repeating unit c).

Preferably, the anion is chloride, bromide, fluoride, iodide, acetate, trifluoroacetate, carbonate, bicarbonate, sulfate, bisulfate, C1-C10 alkylsulfate, C1-C6 alkylsulfonate, C6-C10 arylsulfonate, nitrate, hydrogen phosphate, dihydrogen phosphate, orthophosphate, oxalate, fumarate, ascorbate, citrate, gluconate, lactate, formate, tartrate, succinate, mandelate, p-toluenesulfonate, carboxylate, saccharate, benzoate, or a mixture thereof.

More preferably, the anion is chloride, bromide, acetate, sulfate, trifluoroacetate, methanesulphonate, orthophosphate or, nitrate, or a mixture thereof.

Preferably, the weight average molecular weight (Mw) of the neutral salt of the invention is up to 2500 kDa, more preferably up to 250 kDa-1500 kDa, and even more preferably up to 400 kDa-900 kDa.

Preferably, the number average molecular weight (Mn) of the neutral salt of the invention is up to 2000 kDa, more preferably up to 100 kDa-1000, and even more preferably up to 200 kDa-500 kDa.

In certain embodiments, said neutral salt consisting of a polyaminosaccharide cation and an anion is as described above, with the proviso that:
when the repeating unit c) is between 50 and 70%, R is lactose, and the anion is chloride, then the polyaminosaccharide cation is not obtained from of 200-400 kDa chitosan with a residual degree of acetylation of approximately 15%.

In another aspect, the present invention concerns a process for the preparation of the neutral salt consisting of a polyaminosaccharide cation and an anion, said process comprising the following steps:
i) providing a polyaminosaccharide polymer consisting of repeating units a) and b),
ii) reacting said polyaminosaccharide polymer with a monosaccharide, disaccharide, or oligosaccharide, in aqueous solution,
iii) adding an amino-borane,
iv) adding an acid down to a pH below 4, v) adding an organic solvent, thus precipitating the neutral salt, and vi) separating the precipitated neutral salt.

It has surprisingly been observed that the amino-borans present a remarkable selectivity in the reduction of the imino group compared with the carbonyl group and are compatible with the aqueous environment; at the same time, the formation of a salt owing to the reaction with an acid reduces the time needed for purification of the final product and to neutralise the excess hydride ions, thereby advantageously avoiding the use of bacteriostatic agents. Therefore, the process as a whole offers the advantage of an improved acceptability from a medical and pharmaceutical point of view, since the purity of the final product has been significantly increased, as well as the overall rapidity of the preparation.

Preferably, said polyaminosaccharide polymer consists of 5%-95% repeating unit a) and 95%-5% repeating unit b).

Said monosaccharide, disaccharide, or oligosaccharide corresponds to the definition given above for the moiety R.

Preferably, the aqueous solution of step ii) is an aqueous solution of 0.5-5 wt % acetic acid, more preferably 0.5-2.5 wt %.

Said amino-borane is preferably 2-methylpyridine borane, 5-ethyl-2-methylpyridine borane, pyridine borane, trimethylamine borane, triethylamine borane, dimethylamine borane, tert-butylamine borane, o a mixture thereof. More preferably, said amino-borane is 2-methylpyridine borane, 5-ethyl-2-methylpyridine borane, or a mixture thereof.

The amino-boranes may be used as such or may be previously solubilised or dispersed in water-miscible organic solvents, such as alcohols. The most preferred alcohols are methanol, ethanol, 2-propanol, or a mixture thereof.

The term "acid" means the corresponding acid of the anion described above.

The term "organic solvent" means an organic water-miscible solvent capable of lowering the dielectric constant of the aqueous reaction solution. Suitable organic solvents are acetone, methanol, ethanol, 2-propanol, or a mixture thereof, and preferably the organic solvent is 2-propanol.

Optionally, the precipitate separated in step vi) is washed with mixtures of water and organic solvent, water being in percentages of up to 60%, more preferably up to 40%.

Preferably, the molar ratio of monosaccharide, disaccharide, or oligosaccharide and the repeating unit b) of the polyaminosaccharide polymer is from 0.5 to 30, more preferably from 1 to 20, and even more preferably from 1 to 5.

Preferably, the molar ratio of amino-borane to the repeating unit b) of the polyaminosaccharide polymer is 0.75 to 20, more preferably 1 to 10, and even more preferably 1 to 3.

In a further aspect, the present invention relates to the use of said neutral salt as a medicament.

In a further aspect, the present invention concerns the use of said neutral salt as a biomaterial or a scaffold for cell growth.

In a still further aspect, the present invention relates to a pharmaceutical composition comprising at least a neutral salt consisting of a polyaminosaccharide cation and an anion, as described above, and a bioactive substance selected from collagen, fibrinogen, fibrin, alginic acid, sodium alginate, potassium alginate, magnesium alginate, cellulose, chondroitin sulfate, dermatan sulfate, keratan sulfate, heparin, heparan sulfate, laminin, fibronectin, elastin, polylactic acid, polyglycolic acid, poly(lactic-co-glycolic acid), polycaprolactone, gelatin, albumin, poly(glycolide-co-caprolactone), poly(glycolide-co-trimethylene carbonate), hydroxyapatite, tricalcium phosphate, dicalcium phosphate, demineralized bone matrix, and mixtures thereof.

Preferably, said neutral salt and said bioactive substance are in a weight ratio of 10:1 to 1:50.

Preferably, the pharmaceutical composition of the invention comprises up to 10 wt % of said neutral salt, based on the weight of the pharmaceutical composition, and more preferably, up to 5 wt % of said neutral salt. Particularly preferable are pharmaceutical compositions wherein the amount of said neutral salt is 0.5-5 wt %, based on the weight of the composition.

In first preferred embodiments of the pharmaceutical composition, said bioactive substance is selected from collagen, fibrinogen, fibrin, alginic acid, sodium alginate, potassium alginate, magnesium alginate, cellulose, chondroitin sulfate, dermatan sulfate, keratan sulfate, heparin, heparan sulfate, laminin, fibronectin, elastin, polylactic acid, polyglycolic acid, poly(lactic-co-glycolic acid), polycaprolactone, gelatin, albumin, poly(glycolide-co-caprolactone), poly(glycolide-co-trimethylene carbonate), and mixtures thereof. In these embodiments, the amount of said neutral salt is preferably higher than or equal to that of said bioactive substance. In these embodiments, preferably, said neutral salt and said bioactive substance are in a weight ratio of 5:1 to 1:1, preferably 4:1 to 1:1, and more preferably 3:1 to 1:1.

Said first embodiments are further preferred when the active substance is selected from heparin, chondroitin sulfate, collagen, sodium alginate, potassium alginate, magnesium alginate, and mixtures thereof.

In preferred second embodiments of the pharmaceutical composition, said bioactive substance is selected from hydroxyapatite, tricalcium phosphate, dicalcium phosphate, demineralized bone matrix, and mixtures thereof. In these embodiments, the amount of said neutral salt is preferably less than or equal to that of said bioactive substance. In these embodiments, preferably, said neutral salt and said bioactive substance are in a weight ratio of 1:10 to 1:45, preferably 1:20 to 1:40, and more preferably 1:25 to 1:35.

Said second embodiments are further preferred when the active substance is selected from hydroxyapatite and tricalcium phosphate and mixtures thereof.

In particularly preferred embodiments, the present invention relates to a pharmaceutical composition comprising at least a neutral salt consisting of a polyaminosaccharide cation and an anion, as described above, and hydroxyapatite. Said compositions find advantageous use in orthopaedic applications concerning the skeletal system.

The pharmaceutical composition may be administered via oral, intramuscular, intravenous, intra-articular, transdermal, subdermal, or topical external or internal route, for example surgically.

Preferably, said pharmaceutical composition is administered via intra-articular, transdermal, or topical internal route.

The pharmaceutical composition may further comprise pharmaceutically acceptable excipients.

Suitable pharmaceutically acceptable excipients are, for example, pH regulators, isotonic regulators, solvents, stabilisers, chelating agents, diluents, binders, disintegrators, lubricants, glidants, colorants, suspending agents, surfactants, cryoprotectants, preservatives, and antioxidants.

The present invention also relates to a biomaterial comprising the neutral salt, as described above, either alone or in combination with at least one of the active substances described above. Said biomaterial may be in the form of microspheres, nanospheres, membranes, sponge, wire, film, gauze, guide conduits, hydrogels, fabrics, non-woven fabrics, or a combination thereof.

It should be understood that all the aspects identified as preferred and advantageous for the neutral salt should be deemed to be equally preferred and advantageous also for the preparation process, the compositions, the biomaterials, and the uses stated above.

It should also be understood that all the possible combinations of the preferred aspects of the neutral salt, the preparation process, the compositions, the biomaterials, and the uses stated above are described herein and therefore are also preferred.

Below are working examples of the present invention provided for illustrative purposes.

EXAMPLES

General Procedure for the Preparation Process:

A monosaccharide, disaccharide, or oligosaccharide (0.30-0.20 M), water, acetic acid (0.10-0.20 M) and chitosan having 5% to 20% repeating units a) (0.10 M) were loaded into a reactor. The mixture thus obtained was heated to 60° C. for 2 hours. Then, under the same conditions, the aminoborane (0.10-0.25 M) was added gradually, after being dispersed in an alcohol (10-20%), and the system was left under stirring at 60° C. for 2 hours. Subsequently, an aqueous solution of acid (2-4 N) was added dropwise until a pH of about 2 was reached. Then, the system was cooled to room temperature and the product was precipitated by adding an organic solvent; the precipitate was decanted, the supernatant removed, and the solid moiety washed a first time with a (30:70) water:organic solvent mixture, and then several times with a (15:85) water:organic solvent mixtures, and a final time with organic solvent. Finally, the solid thus obtained was dried under reduced pressure and controlled temperature conditions.

Example 1

Lactose (36 g), water (400 mL), acetic acid (100%), and chitosan (12 g) were loaded into a reactor and the mixture thus obtained heated to 60° C. for 2 hours. Then, under the same conditions, 2-methylpyridine borane (8 g) previously dispersed in methanol (50 mL) was gradually added and the system was left under stirring at 60° C. for 2 hours. Subsequently, an aqueous solution of hydrochloric acid (4 N) was added dropwise until a pH of about 2 was reached. Then, the system was cooled to room temperature and the product was precipitated by adding 2-propanol. Subsequently, the precipitate was decanted, the supernatant removed, and the solid moiety washed a first time with a (30:70) water:2-propanol mixture, and then several times with a (15:85) water:2-propanol mixtures, and a final time with 2-propanol. Finally, the solid thus obtained was dried under reduced pressure and controlled temperature conditions.

Example 2

Lactose (22 g), water (400 mL), acetic acid (100%), and chitosan (12 g) were loaded into a reactor and the mixture thus obtained heated to 60° C. for 2 hours. Then, under the same conditions, 2-methylpyridine borane (8 g) previously dispersed in methanol (50 mL) was gradually added and the system was left under stirring at 60° C. for 2 hours. Subsequently, an aqueous solution of hydrochloric acid (4 N) was added dropwise until a pH of about 2 was reached. Then, the system was cooled to room temperature and the product was precipitated by adding 2-propanol. Subsequently, the precipitate was decanted, the supernatant removed, and the solid moiety washed a first time with a (30:70) water:2-propanol mixture, and then several times with a (15:85) water:2-propanol mixtures, and a final time with 2-propanol. Finally, the solid thus obtained was dried under reduced pressure and controlled temperature conditions.

Example 3

Lactose (36 g), water (400 mL), acetic acid (100%), and chitosan (12 g) were loaded into a reactor and the mixture thus obtained heated to 60° C. for 2 hours. Then, under the same conditions, 2-methylpyridine borane (14 g) previously dispersed in methanol (80 mL) was gradually added and the system was left under stirring at 60° C. for 2 hours. Subsequently, an aqueous solution of hydrochloric acid (4 N) was added dropwise until a pH of about 2 was reached. Then, the system was cooled to room temperature and the product was precipitated by adding 2-propanol. Subsequently, the precipitate was decanted, the supernatant removed, and the solid moiety washed a first time with a (30:70) water:2-propanol mixture, and then several times with a (15:85) water:2-propanol mixtures, and a final time with 2-propanol. Finally, the solid thus obtained was dried under reduced pressure and controlled temperature conditions.

Example 4

Lactose (36 g), water (500 mL), acetic acid (100%), and chitosan (12 g) were loaded into a reactor and the mixture thus obtained heated to 60° C. for 2 hours. Then, under the same conditions, 2-methylpyridine borane (8 g) previously dispersed in methanol (80 mL) was gradually added and the system was left under stirring at 60° C. for 2 hours. Subsequently, an aqueous solution of hydrochloric acid (4 N) was added dropwise until a pH of about 2 was reached. Then, the system was cooled to room temperature and the product was precipitated by adding 2-propanol. Subsequently, the precipitate was decanted, the supernatant removed, and the solid moiety washed a first time with a (30:70) water:2-propanol mixture, and then several times with a (15:85) water:2-propanol mixtures, and a final time with 2-propanol. Finally, the solid thus obtained was dried under reduced pressure and controlled temperature conditions.

Example 5

Lactose (36 g), water (500 mL), acetic acid (100%), and chitosan (12 g) were loaded into a reactor and the mixture thus obtained heated to 60° C. for 2 hours. Then, under the same conditions, 2-methylpyridine borane (8 g) previously dispersed in methanol (80 mL) was gradually added and the system was left under stirring at 60° C. for 2 hours. Subsequently, an aqueous solution of hydrochloric acid (4 N) was added dropwise until a pH of about 2 was reached. Then, the system was cooled to room temperature and the product was precipitated by adding acetone. Subsequently, the precipitate was decanted, the supernatant removed, and the solid moiety washed a first time with a (20:80) water:methanol mixture, and then several times with a (10:90) water:methanol mixtures, and a final time with methanol. Finally, the solid thus obtained was dried under reduced pressure and controlled temperature conditions.

Example 6

Lactose (36 g), water (500 mL), acetic acid (100%), and chitosan (12 g) were loaded into a reactor and the mixture thus obtained heated to 60° C. for 2 hours. Then, under the same conditions, 2-methylpyridine borane (8 g) previously dispersed in methanol (80 mL) was gradually added and the system was left under stirring at 60° C. for 2 hours. Subsequently, an aqueous solution of hydrochloric acid (4 N) was added dropwise until a pH of about 2 was reached. Then, the system was cooled to room temperature and the product was precipitated by adding acetone. Subsequently, the precipitate was decanted, the supernatant removed, and the solid moiety washed a first time with a (25:75) water:ethanol mixture, and then several times with a (15:85) water:ethanol mixtures, and a final time with ethanol. Finally, the solid thus obtained was dried under reduced pressure and controlled temperature conditions.

Example 7

Lactose (36 g), water (400 mL), acetic acid (100%), and chitosan (12 g) were loaded into a reactor and the mixture thus obtained heated to 60° C. for 2 hours. Then, under the same conditions, 2-methylpyridine borane (8 g) previously dispersed in methanol (50 mL) was gradually added and the system was left under stirring at 60° C. for 2 hours. Subsequently, an aqueous solution of sulfuric acid (2 N) was added dropwise until a pH of about 2 was reached. Then, the system was cooled to room temperature and the product was precipitated by adding 2-propanol. Subsequently, the precipitate was decanted, the supernatant removed, and the solid moiety washed a first time with a (30:70) water:2-propanol mixture, and then several times with a (15:85) water:2-propanol mixtures, and a final time with 2-propanol. Finally, the solid thus obtained was dried under reduced pressure and controlled temperature conditions.

Example 8

Lactose (36 g), water (400 mL), acetic acid (100%), and chitosan (12 g) were loaded into a reactor and the mixture thus obtained heated to 60° C. for 2 hours. Then, under the same conditions, 2-methylpyridine borane (8 g) previously dispersed in methanol (50 mL) was gradually added and the system was left under stirring at 60° C. for 2 hours. Subsequently, an aqueous solution of orthophosphoric acid (2 N) was added dropwise until a pH of about 2 was reached. Then, the system was cooled to room temperature and the product was precipitated by adding 2-propanol. Subsequently, the precipitate was decanted, the supernatant removed, and the solid moiety washed a first time with a (30:70) water:2-propanol mixture, and then several times with a (15:85) water:2-propanol mixtures, and a final time with 2-propanol. Finally, the solid thus obtained was dried under reduced pressure and controlled temperature conditions.

Example 9

Lactose (36 g), water (400 mL), acetic acid (100%), and chitosan (12 g) were loaded into a reactor and the mixture thus obtained heated to 60° C. for 2 hours. Then, under the same conditions, 2-methylpyridine borane (8 g) previously dispersed in methanol (50 mL) was gradually added and the system was left under stirring at 60° C. for 2 hours. Subsequently, an aqueous solution of trifluoroacetic acid (4 N) was added dropwise until a pH of about 2 was reached. Then, the system was cooled to room temperature and the product was precipitated by adding 2-propanol. Subsequently, the precipitate was decanted, the supernatant removed, and the solid moiety washed a first time with a (30:70) water:2-propanol mixture, and then several times with a (15:85) water:2-propanol mixtures, and a final time with 2-propanol. Finally, the solid thus obtained was dried under reduced pressure and controlled temperature conditions.

Example 10

Lactose (36 g), water (400 mL), acetic acid (100%), and chitosan (12 g) were loaded into a reactor and the mixture thus obtained heated to 60° C. for 2 hours. Then, under the same conditions, 2-methylpyridine borane (8 g) previously dispersed in methanol (50 mL) was gradually added and the system was left under stirring at 60° C. for 2 hours. Subsequently, an aqueous solution of methanesulfonic acid (4 N) was added dropwise until a pH of about 2 was reached. Then, the system was cooled to room temperature and the product was precipitated by adding 2-propanol. Subsequently, the precipitate was decanted, the supernatant removed, and the solid moiety washed a first time with a (30:70) water:2-propanol mixture, and then several times with a (15:85) water:2-propanol mixtures, and a final time with 2-propanol. Finally, the solid thus obtained was dried under reduced pressure and controlled temperature conditions.

Example 11

Lactose (36 g), water (400 mL), acetic acid (100%), and chitosan (12 g) were loaded into a reactor and the mixture thus obtained heated to 60° C. for 2 hours. Then, under the same conditions, 5-ethyl-2-methylpyridine borane (10 g) previously dispersed in methanol (50 mL) was gradually added and the system was left under stirring at 60° C. for 2 hours. Subsequently, an aqueous solution of hydrochloric acid (4 N) was added dropwise until a pH of about 2 was reached. Then, the system was cooled to room temperature and the product was precipitated by adding 2-propanol. Subsequently, the precipitate was decanted, the supernatant removed, and the solid moiety washed a first time with a (30:70) water:2-propanol mixture, and then several times with a (15:85) water:2-propanol mixtures, and a final time with 2-propanol. Finally, the solid thus obtained was dried under reduced pressure and controlled temperature conditions.

Example 12

Galactose (20 g), water (400 mL), acetic acid (100%), and chitosan (12 g) were loaded into a reactor and the mixture thus obtained heated to 60° C. for 2 hours. Then, under the same conditions, 2-methylpyridine borane (8 g) previously dispersed in methanol (50 mL) was gradually added and the system was left under stirring at 60° C. for 2 hours. Subsequently, an aqueous solution of hydrochloric acid (4 N) was added dropwise until a pH of about 2 was reached. Then, the system was cooled to room temperature and the product was precipitated by adding 2-propanol. Subsequently, the precipitate was decanted, the supernatant removed, and the solid moiety washed a first time with a (30:70) water:2-propanol mixture, and then several times with a (15:85) water:2-propanol mixtures, and a final time with 2-propanol. Finally, the solid thus obtained was dried under reduced pressure and controlled temperature conditions.

Results

Table 1 summarises the chemical and physical characteristics of the salts obtained in Examples 1-12 above. The polysaccharide derivatives were obtained with advantageous yields, easy modification of the degree of substitution, and a high degree of purity. The corresponding percentages, in the three different repeating units, of the polyaminosaccharide cation was determined by $^1$H-NMR analysis, as reported in the literature (N. D'Amelio et al. J. Phys. Chem. B 2013, 117, 13578).

TABLE 1

| EXAMPLES | Yield (g) | CATION | ANION | Boron moiety (ppm) | Ammine moiety (ppm) |
|---|---|---|---|---|---|
| 1 | 27 | a = 8%; b = 32%; c = 60% | [Cl]$^-$ | <50 | <50 |
| 2 | 19 | a = 10%; b = 63%; c = 27% | [Cl]$^-$ | <50 | <50 |
| 3 | 32 | a = 9%; b = 9%; c = 82% | [Cl]$^-$ | <50 | <50 |
| 4 | 27 | a = 8%; b = 37%; c = 55% | [Cl]$^-$ | <50 | <50 |
| 5 | 28 | a = 9%; b = 30%; c = 61% | [Cl]$^-$ | <50 | <50 |
| 6 | 26 | a = 15%; b = 27%; c = 56% | [Cl]$^-$ | <50 | <50 |
| 7 | 28 | a = 12%; b = 29%; c = 59% | [SO$_4$]$^{2-}$ | <50 | <50 |
| 8 | 31 | a = 10%; b = 30%; c = 60% | [H$_2$PO$_4$]$^-$ | <50 | <50 |
| 9 | 32 | a = 8%; b = 35%; c = 57% | [CF$_3$COO]$^-$ | <50 | <50 |
| 10 | 31 | a = 17%; b = 21%; c = 62% | [CH$_3$SO$_3$]$^-$ | <50 | <50 |
| 11 | 27 | a = 15%; b = 22%; c = 63% | [Cl]$^-$ | <50 | <50 |
| 12 | 23 | a = 11 %; b = 0%; c = 89% | [Cl]$^-$ | <50 | <50 |
| 21 | 25 | a = 13%; b = 33%; c = 54% | [Cl]$^-$ | <50 | <50 |
| 22 | 24 | a = 10%; b = 39%; c = 51% | [Cl]$^-$ | <50 | <50 |
| 23 | 27 | a = 10%; b = 29%; c = 61% | [Cl]$^-$ | <50 | <50 |

Example 13

Composition with Polylactic Acid (Neutral Salt 1.00%, Polylactic Acid 0.50%).

The neutral salt obtained in Example 4 (0.630 g) was dissolved in water (25 mL) and the resulting solution mixed at room temperature for 1 hour. Subsequently, a sodium hydroxide solution (2.4 mL, 0.5 N) was added dropwise under the same conditions and the resulting solution mixed for further 30 minutes. Then, the following were added in order, under the same conditions: a 10× solution of PBS (6.30 mL, PBS 10×: Na$_2$HPO$_4$ 81 Mm, NaH$_2$PO$_4$ 17.6 Mm, NaCl 1370 Mm, KCl 27 Mm), water (20 mL), polylactic acid (0.315 g) and water (9.30 mL). The mixture thus obtained was stirred at room temperature until a homogeneous system was obtained.

Example 14

Composition with Collagen (Neutral Salt 1.00%, Collagen 1.00%)

The neutral salt obtained in Example 4 (0.630 g) was dissolved in water (25 mL) and the resulting solution mixed at room temperature for 1 hour. Subsequently, a sodium hydroxide solution (2.4 mL, 0.5 N) was added dropwise under the same conditions and the resulting solution mixed for further 30 minutes. Then, the following were added in order, under the same conditions: a 10× solution of PBS (6.30 mL, PBS 10×: Na$_2$HPO$_4$ 81 Mm, NaH$_2$PO$_4$ 17.6 Mm, NaCl 1370 Mm, KCl 27 Mm), water (20 mL), polylactic acid (0.630 g) and water (9.30 mL). The mixture thus obtained was stirred at room temperature until a homogeneous system was obtained.

Example 15

Composition with Chondroitin Sulfate (Neutral Salt 1.20%, Chondroitin Sulfate 0.40%)

The neutral salt obtained in Example 4 (0.756 g) was dissolved in water (25 mL) and the resulting solution mixed at room temperature for 1 hour. Subsequently, a sodium hydroxide solution (2.88 mL, 0.5 N) was added dropwise under the same conditions and the resulting solution mixed for further 30 minutes. Then, the following were added in order, under the same conditions: a 10× solution of PBS (6.30 mL, PBS 10×: Na$_2$HPO$_4$ 81 Mm, NaH$_2$PO$_4$ 17.6 Mm, NaCl 1370 Mm, KCl 27 Mm), water (20 mL), chondroitin sulfate (0.252 g) and water (8.82 mL). The mixture thus obtained was stirred at room temperature until the chondroitin sulfate was completely dissolved.

Example 16

Composition with Poly(Lactic-Co-Glycolic) Acid or PLGA (Neutral Salt 1.80%, PGLA 1.00%).

The neutral salt obtained in Example 4 (1.134 g) was dissolved in water (25 mL) and the resulting solution mixed at room temperature for 1 hour. Subsequently, a sodium hydroxide solution (4.32 mL, 0.5 N) was added dropwise under the same conditions and the resulting solution mixed for further 30 minutes. Then, the following were added in order, under the same conditions: a 10× solution of PBS (6.30 mL, PBS 10×: Na$_2$HPO$_4$ 81 Mm, NaH$_2$PO$_4$ 17.6 Mm, NaCl 1370 Mm, KCl 27 Mm), water (20 mL), PLGA (0.630 g) and water (7.38 mL). The mixture thus obtained was stirred at room temperature until a homogeneous system was obtained.

Example 17

Composition with Elastin (Neutral Salt 0.75%, Elastin 0.25%)

The neutral salt obtained in Example 4 (0.473 g) was dissolved in water (25 mL) and the resulting solution mixed at room temperature for 1 hour. Subsequently, a sodium hydroxide solution (1.80 mL, 0.5 N) was added dropwise under the same conditions and the resulting solution mixed for further 30 minutes. Then, the following were added in order, under the same conditions: a 10× solution of PBS (6.30 mL, PBS 10×: Na$_2$HPO$_4$ 81 Mm, NaH$_2$PO$_4$ 17.6 Mm, NaCl 1370 Mm, KCl 27 Mm), water (20 mL), elastin (0.158 g) and water (11.10 mL). The mixture thus obtained was stirred at room temperature until a homogeneous system was obtained.

Example 18

Composition with Potassium Alginate (Neutral Salt 1.00%, Potassium Alginate 0.75%)

The neutral salt obtained in Example 4 (0.630 g) was dissolved in water (25 mL) and the resulting solution mixed at room temperature for 1 hour. Subsequently, a sodium hydroxide solution (2.40 mL, 0.5 N) was added dropwise under the same conditions and the resulting solution mixed for further 30 minutes. Then, the following were added in order, under the same conditions: a 10× solution of PBS (6.30 mL, PBS 10×: Na$_2$HPO$_4$ 81 Mm, NaH$_2$PO$_4$ 17.6 Mm, NaCl 1370 Mm, KCl 27 Mm), water (20 mL), potassium alginate (0.473 g) and water (9.30 mL). The mixture thus obtained was stirred at room temperature until the potassium alginate completely dissolved.

Example 19

Composition with Hydroxyapatite in Tricalcium Phosphate (Neutral Salt 1.94%, Hydroxyapatite 1.78%, Tricalcium Phosphate 57.58%)

The neutral salt obtained in Example 4 (0.163 g) was placed in water (2.64 mL) and mixed at room temperature for 1 hour and at 60° C. for 2 hours; subsequently, a sodium hydroxide solution (0.62 mL, 0.5 N) was added dropwise under the same conditions and the resulting solution mixed for further 30 minutes. The solution thus obtained was then transferred, at room temperature, to a beaker containing hydroxyapatite (0.150 g) homogeneously dispersed in tricalcium phosphate (4.850 g). The liquid phase and the solid phase were then intimately mixed until a cement paste was obtained.

Example 20

Composition with Tricalcium Phosphate in Hydroxyapatite (Neutral Salt 1.94%, Tricalcium Phosphate 1.78%, Hydroxyapatite 57.58%)

The neutral salt obtained in Example 4 (0.163 g) was placed in water (2.64 mL) and mixed at room temperature for 1 hour and at 60° C. for 2 hours; subsequently, a sodium hydroxide solution (0.62 mL, 0.5 N) was added dropwise under the same conditions and the resulting solution mixed for further 30 minutes. The solution thus obtained was then transferred, at room temperature, to a beaker containing tricalcium phosphate (0.150 g) homogeneously dispersed in hydroxyapatite (4.850 g). The liquid phase and the solid phase were then intimately mixed until a cement paste was obtained.

Example 21

Lactose (36 g), water (500 mL), acetic acid (100%), with a pH value of up to approximately 5.5, and chitosan (12 g) were loaded into a reactor and the mixture thus obtained heated to 60° C. for 2 hours. Then, under the same conditions, 2-methylpyridine borane (7 g) previously dispersed in methanol (50 mL) was gradually added and the system was left under stirring at 60° C. for 5 hours. Subsequently, an aqueous solution of hydrochloric acid (4 N) was added dropwise until a pH of about 2 was reached. Then, the system was cooled to room temperature and the product was precipitated by adding 2-propanol. Subsequently, the precipitate was decanted, the supernatant removed, and the solid moiety washed a first time with a (20:80) water:2-propanol mixture, and then several times with a (10:90) water:2-propanol mixtures, and a final time with 2-propanol. Finally, the solid thus obtained was dried under reduced pressure and controlled temperature conditions.

Example 22

Chitosan (12 g), water (400 mL), and acetic acid (100%), with a pH value of up to approximately 5.5, were loaded into a reactor and the mixture thus obtained mixed at room temperature for 2 hours. Then, under the same conditions, lactose (36 g) previously dissolved in water (200 mL) was added and the mixture was heated to 60° C. Subsequently, 2-methylpyridine borane (7 g) previously dispersed in methanol (50 mL) was gradually added and the system was left under stirring at 60° C. for 5 hours. Subsequently, an aqueous solution of hydrochloric acid (4 N) was added dropwise until a pH of about 2 was reached. Then, the system was cooled to room temperature and the product was precipitated by adding 2-propanol. Subsequently, the precipitate was decanted, the supernatant removed, and the solid moiety washed a first time with a (20:80) water:2-propanol mixture, and then several times with a (10:90) water:2-propanol mixtures, and a final time with 2-propanol. Finally, the solid thus obtained was dried under reduced pressure and controlled temperature conditions.

Example 23

Chitosan (12 g), water (400 mL), and acetic acid (100%), with a pH value of up to approximately 6, were loaded into a reactor and the mixture thus obtained mixed at room temperature for 2 hours. Then, under the same conditions, lactose (36 g) previously dissolved in water (200 mL) was added and the mixture was heated to 60° C.

Subsequently, under the same conditions, 2-methylpyridine borane (7 g) previously dispersed in methanol (50 mL) was gradually added and the system was left under stirring at 60° C. for 2 hours. Subsequently, an aqueous solution of hydrochloric acid (4 N) was added dropwise until a pH of about 2 was reached. Then, the system was cooled to room temperature and the product was precipitated by adding 2-propanol. Subsequently, the precipitate was decanted, the supernatant removed, and the solid moiety washed the first two times with a (20:80) water:2-propanol mixture, and then several times with a (10:90) water:2-propanol mixtures, and a final time with 2-propanol. Finally, the solid thus obtained was dried under reduced pressure and controlled temperature conditions.

The invention claimed is:

1. Neutral salt in solid form consisting of a polyaminosaccharide cation and an anion, wherein the polyaminosaccharide cation consists of the following three repeating units:

a) up to 25% of

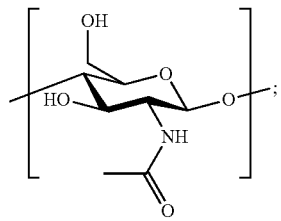

b) less than 65% of c) up to 90% of

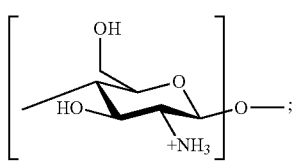

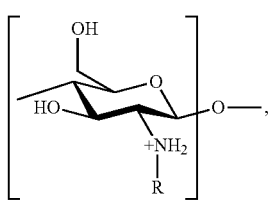

wherein R an aldose or ketose moiety,
wherein the anion is monovalent, bivalent or trivalent, and
wherein the anion is chloride, bromide, fluoride, iodide, acetate, trifluoroacetate, carbonate, bicarbonate, sulfate, bisulfate, C1-C10 alkylsulfate, C1-C6 alkylsulfonate, C6-C10 arylsulfonate, nitrate, hydrogen phosphate, dihydrogen phosphate, orthophosphate, oxalate, fumarate, ascorbate, citrate, gluconate, lactate, formate, tartrate, succinate, mandelate, p-toluenesulfonate, carboxylate, saccharate, benzoate, or a mixture thereof.

2. The neutral salt of claim 1, wherein R is a moiety of formula (1):

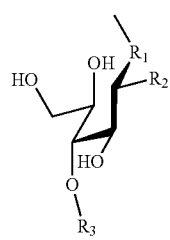

wherein $R_1$ is —$CH_2$— or —CO—,
$R_2$ is —OH, or —$NHCOCH_3$,
$R_3$ is H, monosaccharide, disaccharide, or oligosaccharide,
or R is a moiety of formula (2):

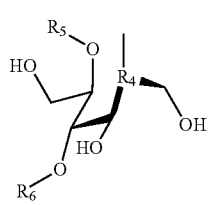

$R_4$ is —CH—,
$R_5$ and $R_6$ are, independently of each other, H, monosaccharide, disaccharide, or oligosaccharide.

3. The neutral salt of claim 2, wherein $R_3$, $R_5$ and $R_6$ are, independently of one another, H, glucose, galactose, arabinose, xylose, mannose, lactose, trealose, gentiobiose, cellobiose, cellotriose, maltose, maltotriose, chitobiose, chitotriose, mannobiose, melibiose, fructose, N-acetyl glucosamine, N-acetylgalactosamine, or a combination thereof.

4. The neutral salt of claim 1, wherein R is a lactose or galactose moiety.

5. The neutral salt of claim 1, wherein, in the polyaminosaccharide cation, the repeating unit a) is present in a percentage of 5% to 20%.

6. The neutral salt of claim 1, wherein, in the polyaminosaccharide cation, the repeating unit b) is present in a percentage of 5% to 45%.

7. The neutral salt of claim 1, wherein, in the polyaminosaccharide cation, the repeating unit c) is present in a percentage of 45% to 90%.

8. The neutral salt of claim 1, wherein the weight average molecular weight of the neutral salt is up to 2500 kDa, or the number average molecular weight of the neutral salt is up to 2000 kDa.

9. A process for the preparation of a neutral salt consisting of a polyaminosaccharide cation and an anion, wherein the polyaminosaccharide cation consists of the following three repeating units:

a) up to 25% of

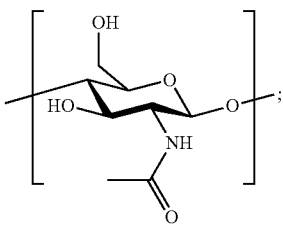

b) less than 65% of

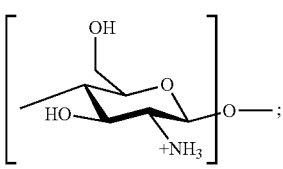

c) up to 90% of

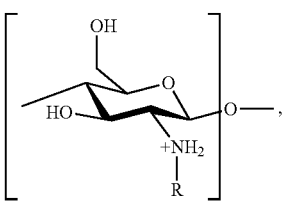

wherein R an aldose or ketose moiety,
wherein the anion is monovalent, bivalent or trivalent, and
wherein the anion is chloride, bromide, fluoride, iodide, acetate, trifluoroacetate, carbonate, bicarbonate, sulfate, bisulfate, C1-C10 alkylsulfate, C1-C6 alkylsulfonate, C6-C10 arylsulfonate, nitrate, hydrogen phosphate, dihydrogen phosphate, orthophosphate, oxalate, fumarate, ascorbate, citrate, gluconate, lactate, formate, tartrate, succinate, mandelate, p-toluenesulfonate, carboxylate, saccharate, benzoate, or a mixture thereof, said process comprising the steps of:
i) providing a polyaminosaccharide polymer consisting of the repeating units a) and b),
ii) reacting said polyaminosaccharide polymer with a monosaccharide, disaccharide, or oligosaccharide, in aqueous solution,
iii) adding an amino-borane,
iv) adding an acid down to pH below 4,
v) adding an organic solvent, thus precipitating the neutral salt, and
vi) separating the precipitated neutral salt.

10. The process of claim 9, wherein said polyaminosaccharide polymer consists of 5%-95% of repeating unit a), and 95%-5% of repeating unit b).

11. The process of claim 9, wherein said amino- borane is 2-methylpyridine borane, 5-ethyl-2-methylpyridine borane, pyridine borane, trimethylamine borane, triethylamine borane, dimethylamine borane, tert-butylamine borane, or a mixture thereof.

12. The process of claim 9, wherein said organic solvent is acetone, methanol, ethanol, 2-propanol, or a mixture thereof.

13. The process of claim 9, wherein the molar ratio between monosaccharide, disaccharide, or oligosaccharide, and repeating unit b) of the polyaminosaccharide polymer is 0.5 to 30, or the molar ratio between amino-borane and repeating unit b) of the polyaminosaccharide polymer is 0.75 to 20.

14. Pharmaceutical composition comprising at least a neutral salt consisting of
a polyaminosaccharide cation and an anion, wherein the polyaminosaccharide cation consists of the following three repeating units:
a) up to 25% of

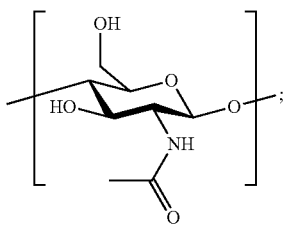

b) less than 65% of

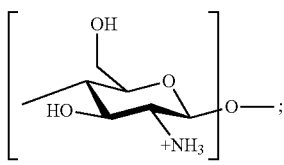

c) up to 90% of

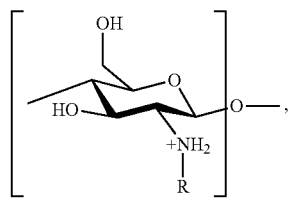

wherein R an aldose or ketose moiety, wherein the anion is monovalent, bivalent or trivalent, wherein the anion is chloride, bromide, fluoride, iodide, acetate, trifluoroacetate, carbonate, bicarbonate, sulfate, bisulfate, C1-C10 alkylsulfate, C1-C6 alkylsulfonate, C6-C10 arylsulfonate, nitrate, hydrogen phosphate, dihydrogen phosphate, orthophosphate, oxalate, fumarate, ascorbate, citrate, gluconate, lactate, formate, tartrate, succinate, mandelate, p-toluenesulfonate, carboxylate, saccharate, benzoate, or a mixture thereof, and a bioactive substance selected from collagen, fibrinogen, fibrin, alginic acid, sodium alginate, potassium alginate, magnesium alginate, cellulose, chondroitin sulfate, dermatan sulfate, keratan sulfate, heparin, heparan sulfate, laminin, fibronectin, elastin, polylactic acid, polyglycolic acid, poly(lactic-co-glycolic acid), polycaprolactone, gelatin, albumin, poly(glycolide-co-caprolactone), poly(glycolide-co-trimethylene carbonate), hydroxyapatite, tricalcium phosphate, dicalcium phosphate, demineralized bone matrix, and mixtures thereof.

15. The pharmaceutical composition of claim 14, wherein said neutral salt and said bioactive substance are in a ratio of 10:1 to 1:50.

16. The pharmaceutical composition of claim 14, wherein said neutral salt and said bioactive substance are in a ratio of 5:1 to 1:1.

17. The pharmaceutical composition of claim 16, wherein said bioactive substance is selected from heparin, chondroitin sulfate, collagen, sodium alginate, potassium alginate, magnesium alginate, and mixtures thereof.

18. The pharmaceutical composition of claim 14, wherein said neutral salt and said bioactive substance are in a ratio of 1:10 to 1:45.

19. The pharmaceutical composition of claim 18, wherein said bioactive substance is selected from hydroxyapatite, tricalcium phosphate, dicalcium phosphate, demineralized bone matrix, and mixtures thereof.

* * * * *